United States Patent
Kawase et al.

(10) Patent No.: US 7,352,449 B2
(45) Date of Patent: Apr. 1, 2008

(54) METHOD AND APPARATUS FOR DETECTING MATERIALS

(75) Inventors: Kodo Kawase, Wako (JP); Yuuki Watanabe, Yonezawa (JP); Tomofumi Ikari, Wako (JP)

(73) Assignees: Riken, Saitama (JP); S-I Seiko Co., Ltd., Ehime (JP)

( * ) Notice: Subject to any disclaimer, the term of this patent is extended or adjusted under 35 U.S.C. 154(b) by 350 days.

(21) Appl. No.: 10/953,465

(22) Filed: Sep. 30, 2004

(65) Prior Publication Data
US 2005/0116170 A1 Jun. 2, 2005

(30) Foreign Application Priority Data
Oct. 3, 2003 (JP) ............................. 2003-345838

(51) Int. Cl.
*G01N 21/00* (2006.01)
(52) U.S. Cl. ........................................ 356/73
(58) Field of Classification Search .................. 356/73
See application file for complete search history.

(56) References Cited

U.S. PATENT DOCUMENTS 6,957,099 B1 * 10/2005 Arnone et al. .............. 600/473

2002/0085209 A1 * 7/2002 Mittleman et al. .......... 356/497
2004/0061055 A1 * 4/2004 Kawase et al. ............. 250/330

FOREIGN PATENT DOCUMENTS

| DE | 10309845 A1 * | 9/2004 |
|---|---|---|
| JP | 10-90174 | 4/1989 |
| JP | 08-320254 | 12/1996 |
| JP | 2001-66375 | 3/2001 |
| WO | 00/50859 | 8/2000 |

* cited by examiner

Primary Examiner—Gregory J. Toatley, Jr.
Assistant Examiner—Kara E Geisel
(74) Attorney, Agent, or Firm—Griffin & Szipl, P.C.

(57) ABSTRACT

An apparatus for detecting materials includes a database for storing detecting spectra of detecting materials, and a tera-hertz wave applying unit for applying tera-hertz waves having a plurality of different frequencies around a boundary between a light wave frequency and a radio wave frequency, to a predetermined position of an inspecting object. The apparatus includes an output wave receiving unit for receiving an output wave that is the tera-hertz wave having been applied to the inspecting object, and a determining unit for determining whether or not the output wave includes the detecting spectrum.

5 Claims, 9 Drawing Sheets

FIG. 1

1 : APPARATUS FOR INSPECTING MATERIALS
9 : INSPECTING OBJECT
E : OUTPUT WAVE

FIG. 2

1: APPARATUS FOR INSPECTING MATERIALS
11: PUMP WAVE INJECTION DEVIECE
20: TERA-HERTZ WAVE GENERATION DEVICE
50: DETECTOR
E: OUTPUT WAVE

FIG. 3

20 :TERA-HERTZ WAVE GENARATION DEVICE

1 : APPARATUS FOR INSPECTING MATERIALS
50 : DETECTOR
53 : DETECTING DEVICE
60 : PERSONAL COMPUTER
80 : INTERFEROMETER

METHOD AND APPARATUS FOR DETECTING MATERIALS

This application claims priority from Japanese Patent Application No. 2003-345838, filed Oct. 3, 2003, the entire disclosure of which is incorporated herein by reference.

BACKGROUND OF THE INVENTION

1. Field of the Invention

The present invention relates to a method and an apparatus for detecting materials put in a container such as an envelope and a plastic bag without breaking the container.

2. Description of the Related Art

Conventionally, an X-ray scanner and a sniffer dog are used for detecting specific materials including banned drug such as a narcotic drug and a stimulant drug, and an explosive such as an RDX and a TNT.

The detecting method using an X-ray scanner and a dog is not advantageous because when opening of the mailed envelope is restricted, the specific materials cannot be detected even if the specific material is contained in the envelope.

Meanwhile, References 1, 2 and 3 (Japanese Laid-Open Patent Publication Nos. 8-320254, 10-90174 and 2001-66375) propose apparatuses that use a tera-hertz wave to detect foreign materials contained in an article without breaking the article.

However, the apparatuses of References 1, 2 and 3 can only detect whether or not foreign materials exist. In addition, these apparatus output an displayed image, so that an operator needs to judge whether the foreign materials exist or not by watching the displayed image.

For this reason, when the operator becomes tired due to continuous watching, there is a risk that the operator misses the foreign material. Thus, the accurate detecting relies on a recognizing ability of the operator depending on concentration, experience, and intuition of the operator.

SUMMARY OF THE INVENTION

It is an object of the present invention to provide an apparatus and a method for detecting materials, by which it is possible to determine whether or not a specific material exists in an article, in a uniform manner at a high speed. Also, it is another object of the present invention to reliably detect a material put in an article that cannot be broken or opened.

According to the present invention, there is provided a method for detecting materials, comprising the steps of: applying tera-hertz waves of a plurality of different frequencies around a boundary between a light wave frequency and a radio wave frequency, to a predetermined position of an inspecting object; and determining whether or not an output wave includes a detecting spectrum of a detecting material, the output wave being the tera-hertz wave that has been applied to the inspecting object.

Further, according to the present invention, there is provided an apparatus for detecting materials, comprising: a database for storing detecting spectra of detecting materials; tera-hertz wave applying means for applying tera-hertz waves having a plurality of different frequencies around a boundary between a light wave frequency and a radio wave frequency, to a predetermined position of an inspecting object; output wave receiving means for receiving an output wave that is the tera-hertz wave having been applied to the inspecting object; and determining means for determining whether or not the output wave includes the detecting spectrum.

The tera-hertz wave applying means for applying tera-hertz waves having a plurality of different frequencies may include a mercury lamp light source of an FTIR (Fourier Transform Infrared Spectrometer), or applying means using a femtosecond laser to generate a tera-hertz wave, and, optionally, applying means that generates white light having a plurality of different frequencies. Alternatively, the tera-hertz wave applying means includes applying means that changes a wavelength of monochromatic light generated from a wavelength changeable light source to produce a plurality of wavelengths. Additionally, when the tera-hertz wave applying means generates white light, the spectrum is preferably obtained by Fourier transformation.

The output wave of the tera-hertz wave that has been applied to the inspecting object includes the tera-hertz wave that has penetrated the inspecting object, and/or the tera-hertz wave that has been reflected by the inspecting object.

By the above configuration, it is possible to reliably determine whether or not one or more inspecting target materials exist in the inspecting object. Particularly, since the tera-hertz waves of a plurality of frequencies are applied to the predetermined position of the inspecting object, it is possible to determine the existence of the detecting target material by the pinpoint measurement at a high speed.

Even if the detecting target material cannot be quantified, use of the tera-hertz wave that has been reflected by the inspecting object enables the detecting target material to be detected on the condition that at least a minute amount of the detecting target material exists (for example, a minute amount of the material is enclosed in the article).

On the other hand, use of the tera-hertz wave that has penetrated the inspecting object enables calculation of the percentage or amount of the detecting target material. It is possible, therefore to perform detailed analysis.

According to one aspect of the present invention, the detecting spectra include a detecting target spectrum of a detecting target material and an adjunct spectrum of an adjunct material.

Thereby, a plastic bag or the like that contains a drug of the detecting target material can be detected as the adjunct material together with this drug. Accordingly, the detecting target material can be precisely distinguished from the adjunct material to improve the accuracy in detecting the detecting target material.

Further, according to another aspect of the present invention, the tera-hertz wave applying means includes white light applying means for applying white light of a plurality of different frequencies, and the material detecting apparatus further includes spectrum obtaining means for performing Fourier transformation on the output wave to obtain a spectrum formed by the respective different frequencies.

The white light applying means may include an irradiation device of the FTIR, or an irradiation device that has a femtosecond laser.

The spectrum obtaining means may be constituted by a detector that detects the output wave, and a computer that performs arithmetic operation such as Fourier transformation.

By the above-described configuration, it is possible to simultaneously apply the light including a plurality of frequencies to the inspecting object. Thereby, high speed detecting operation can be carried out.

Thus, according to the present invention, it is possible to reliably detect a material contained in an article that cannot be broken or opened.

Other objects and advantages of the present invention will become apparent from the following detailed description with reference to the accompanying drawings.

DESCRIPTION OF THE PREFERRED EMBODIMENTS

Embodiments of the present invention will be described with reference to the accompanying drawings.

Figure 1:
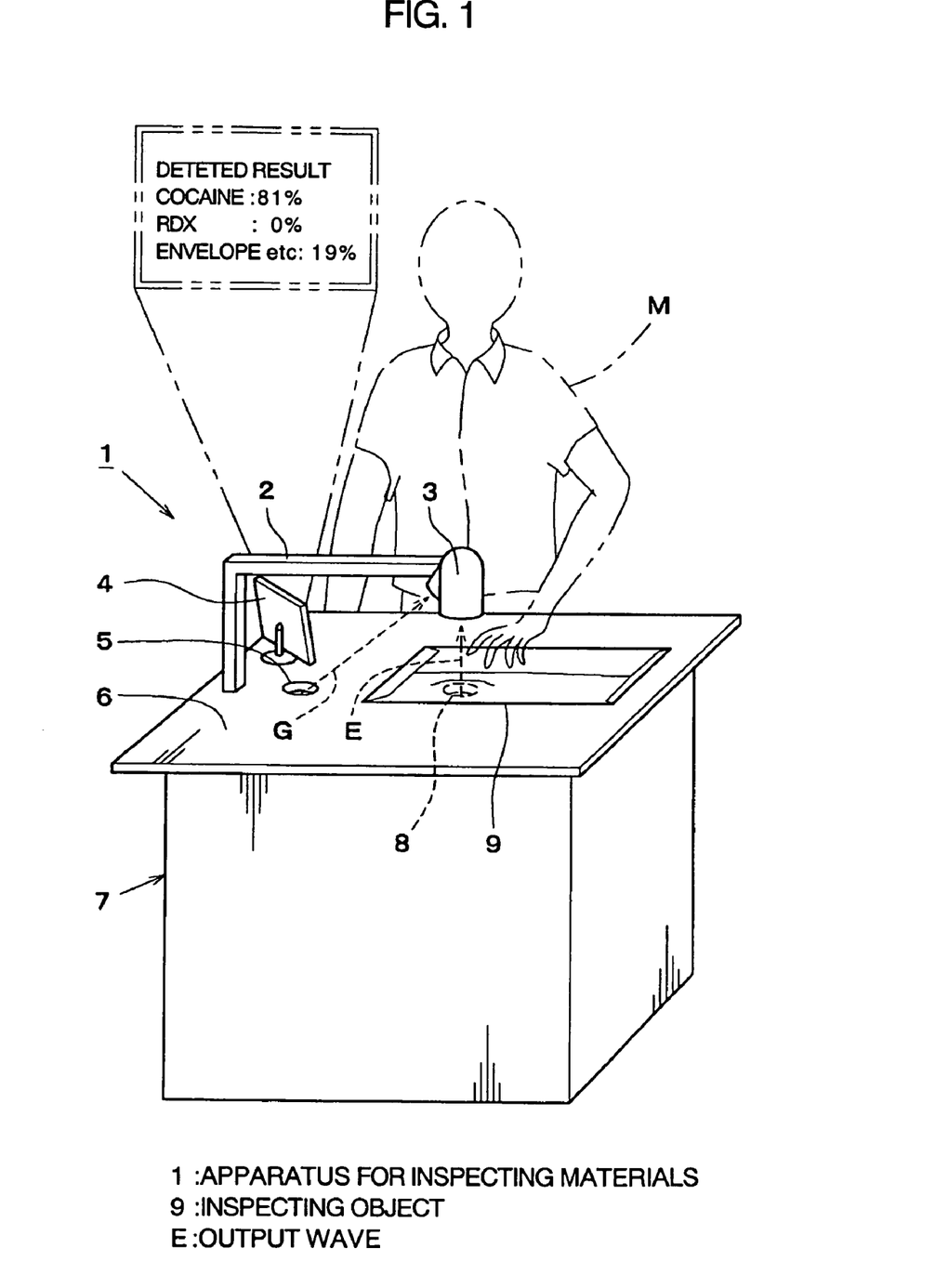
FIG. 1 is a perspective view showing an appearance of an material inspecting apparatus according to a first embodiment of the present invention.

FIG. 1 is a perspective view showing a material inspecting apparatus 1 according to a first embodiment of the present invention. First, the configuration of the material inspecting apparatus 1 will be described.

The material inspecting apparatus 1 includes a table 7 having a board 6 of which plan view is a quadrilateral. The material inspecting apparatus 1 also includes an L-shaped arm 2 of which root portion is fixed at the left part of the table 7 and that extends upwards from the root portion to the level near a waist of an operator M, and at this level, bends towards the right direction to extend up to the center part of the board 6.

Further, the material inspecting apparatus 1 includes a measurement device 3 provided at the front end of the L-shaped arm 2. The measurement device 3 has an approximately cylindrical shape, and measures an output wave (penetration wave) E that has passed through an inspecting object 9, and measures a reference wave G for noise cancellation.

Furthermore, the material inspecting apparatus 1 includes a touch monitor 4 installed on the board 6 at the side of the operator M and at the right part of the operator M. The touch monitor 4 displays a result of the measurement and receives touch operating input. The touch monitor 4 is connected to a personal computer installed inside the table 7.

By the above-described configuration, the operator M can place an inspecting object on the board 6, and perform touch operation on the touch monitor 4 to start the measurement and confirm the result of the measurement. For example, when the inspecting object 9 is an envelope as shown in FIG. 1, a suspicious part that swells is located on a hole 8 of a tera-hertz wave radiating part to perform pinpoint measurement.

Figure 2:
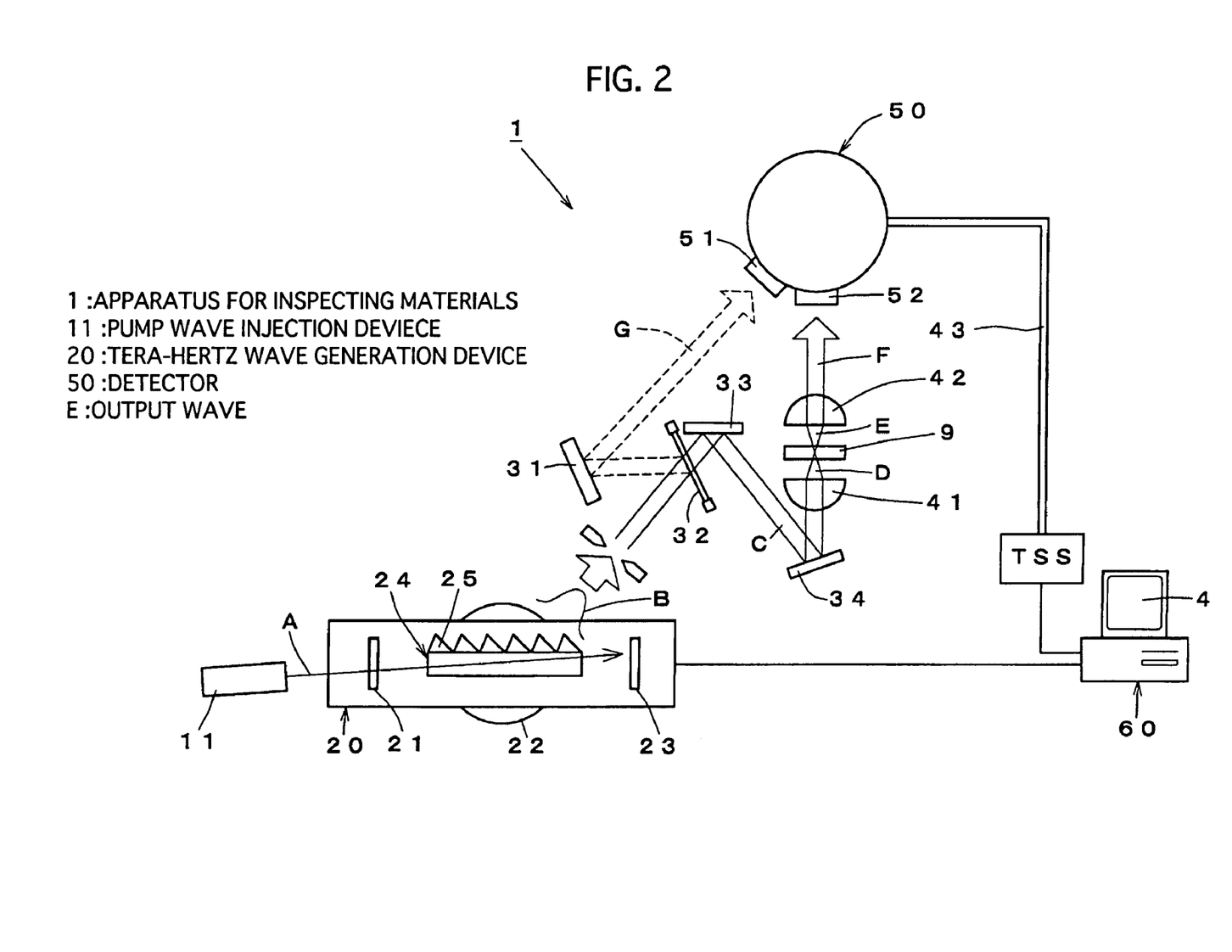
FIG. 2 shows a system configuration of the material inspecting apparatus of FIG. 1.

Next, a system configuration of the material inspecting apparatus 1 will be described with reference to FIG. 2. FIG. 2 shows the system configuration of the material inspecting apparatus 1.

The material inspecting apparatus 1 includes a pump wave injection device 11, a tera-hertz wave generation device 20, a rotation driving device 22, a wire grid 32, a collective lens 41, a dispersion lens 42, a detector 50, and the personal computer 60.

The pump wave injection device 11 provides a pump wave.

The tera-hertz wave generation device 20 includes a resonance mirrors 21, 23 and a nonlinear optical crystal 24 including a prism coupler 25.

The lower half of the resonance mirror 21 is made of transparent glass (transparent part), and the upper half of the resonance mirror 21 is constituted by a mirror (reflection part) of a high-reflectance coat. On the contrary, the upper half of the resonance mirror 23 is made of transparent glass (transparent part), and the lower half of the resonance mirror 21 is constituted by the mirror (reflection part) of the high-reflectance coat.

The resonance mirrors 21 and 23 are arranged such that reflection mirror surfaces of the resonance mirrors 21 and 23 face each other. The nonlinear optical crystal 24 is located at an approximate middle position between the resonance mirrors 21 and 23.

The rotation driving device 22 includes a motor and a gear that rotate the tera-hertz wave generation device 20 by a minute angle so as to change an incident angle of a pump wave to the tera-hertz wave generation device 20.

The wire grid 32 is a dividing device that at a predetermined ratio, divides the tera-hertz wave generated from the tera-hertz wave generation device 20 into an applying wave applied to an inspecting object 9 and a reference wave used for noise cancellation.

The collective lens 41 focuses the tera-hertz wave to apply the focused wave to the inspecting object 9. On the other hand, the dispersion lens 42 increases a diameter of the output wave (tera-hertz wave) that has passed through the inspecting object 9. In this manner, it is possible to reduce to a small area of the inspecting object 9 to which the tera-hertz wave is applied, and to obtain the tera-hertz wave beam of a large diameter that has penetrated the inspecting object 9.

The dispersion lens 42 and the detector 50 are accommodated in the measurement device 3 (refer to FIG. 1). The detector 50 of the measurement device 3 receives from an output wave incident hole 52 the output wave that has passed through the inspecting object 9. Further, the detector 50 receives from a reference wave incident hole 51 the tera-hertz wave that does not have passed through the inspecting object 9. Thus received tera-hertz waves are detected by an Si bolometer or a pyroelectric element provided at the detector 50.

Thereby, it is possible to remove a noise from the generated tera-hertz wave, and to perform appropriate measurement even when the tera-hertz wave generated by the tera-hertz wave generation device 20 contains a noise.

The personal computer 60 includes a control device constituted by a CPU, a ROM and a RAM, a hard disk (storage device) for storing data, and a storage medium reader/writer for reading data from a storage medium and writing data in the storage medium such as a CD-ROM and a flexible disk.

Further, the personal computer 60 includes an interface board to which the detector 50, an input device (a touch panel of the touch monitor 4, a mouse, a keyboard, and the like) that receives input operation, and a displaying device (the touch monitor 4) are connected.

The reflection mirrors 31, 33 and 34 guide the tera-hertz wave to the respective destinations.

The tera-hertz wave generation device 20 receives the pump wave provided by the pump wave injection device 11 to generate the tera-hertz wave B. Then, the tera-hertz wave B is reflected as the applying wave C by the reflection mirrors 33 and 34 to be guided to the collective lens 41. Thereafter, the collective lens 41 focuses the applying wave C so as to be applied to the inspecting object 9 as the focused applying wave D. The output wave E that has been applied to the inspecting object 9 as the applying wave D and has penetrated the inspecting object 9 passes through the dispersion lens 42. Thereby, the diameter of the output wave E can be increased. Then, the detector 50 receives the output wave F from the dispersion lens 42.

Meanwhile, the reference wave G divided from the tera-hertz wave B by the wire grid 32 is reflected by the reflection mirror 31 to enter the detector 50.

In this manner, the tera-hertz wave is applied to the inspecting object 9, penetrates the inspecting object 9, and enters the detector 50 as the output wave F while the reference wave G enters the detector 50 for noise cancellation.

Figure 3:
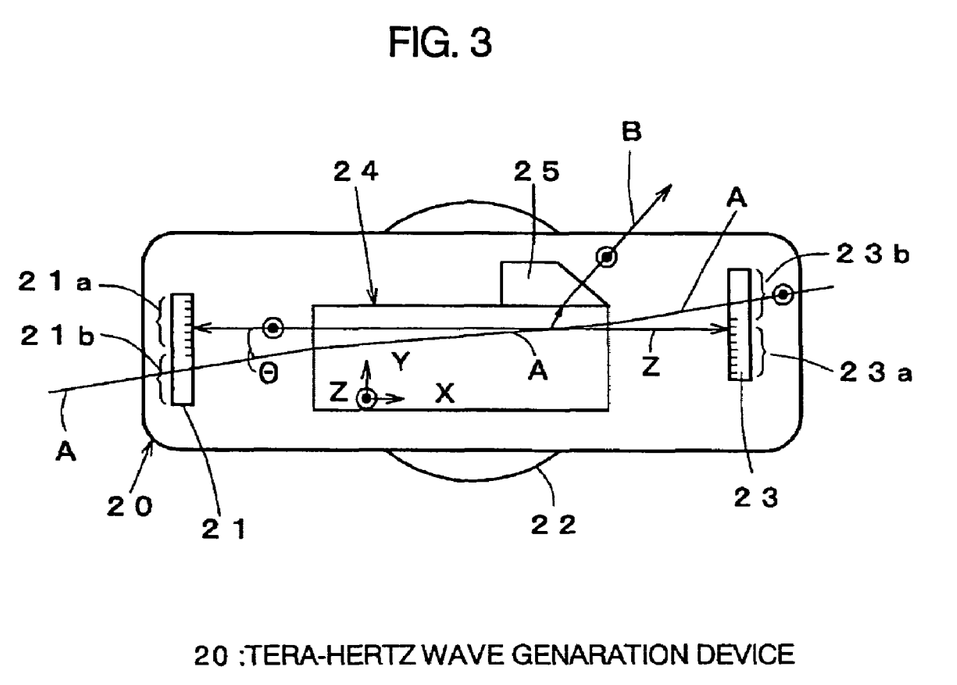
FIG. 3 shows a configuration of a tera-hertz wave generation device.

Next, a principle of generating a tera-hertz wave will be described with reference to FIG. 3. FIG. 3 shows a configuration of the tera-hertz wave generation device 20.

When the pump wave A generated by the pump wave injection device 11 enters the tera-hertz wave generation device 20, the pump wave A passes though the penetration part 21b of the resonance mirror 21, and then enters the nonlinear optical crystal 24. The pump wave A is refracted by the nonlinear optical crystal 24, and then penetrates the penetrating part 23b of the resonance mirror 23.

Intensity of a broad idler wave Z is raised by the reflection parts 21a and 23a of the resonance mirrors 21 and 23 constituting a resonator. This resonator is directed in a specific direction shifted from the traveling direction of the idler wave Z by a predetermined angle θ such that the intensity of the idler wave in the specific direction can be raised.

The tera-hertz wave generated by the above-described configuration and function is brought to the outside of the tera-hertz wave generation device 20 by the prism coupler 25.

By the above-described configuration and function, the tera-hertz wave generation device 20 can exhibit a parametric effect so that the tera-hertz wave B having necessary intensity can be extracted from the pump wave A, and brought to the outside.

Furthermore, the tera-hertz wave generation device 20 can be gradually rotated by the rotation driving device 22 so as to change an incident angle of the pump wave A.

When the incident angle of the pump wave A is changed, an angle made by the traveling direction of the pump wave A and the traveling direction of the idler wave Z in the nonlinear optical crystal 24 is changed, and the angle made by the traveling direction of the tera-hertz wave B and the traveling direction of the idler wave Z is also changed.

This phase matching condition change enables a wavelength of the tera-hertz wave B to be changed, achieving continuous wavelength changing. Thus, the rotation driving device 22 functions as a device for changing a wavelength of the tera-hertz wave B.

According to the first embodiment of the present invention, it is possible to change a wavelength of the tera-hertz wave B from about 600 micron meters to about 60 micron meters. In other words, it is possible to change a frequency of the tera-hertz wave from 0.5 THz to 5 THz.

Figure 4:
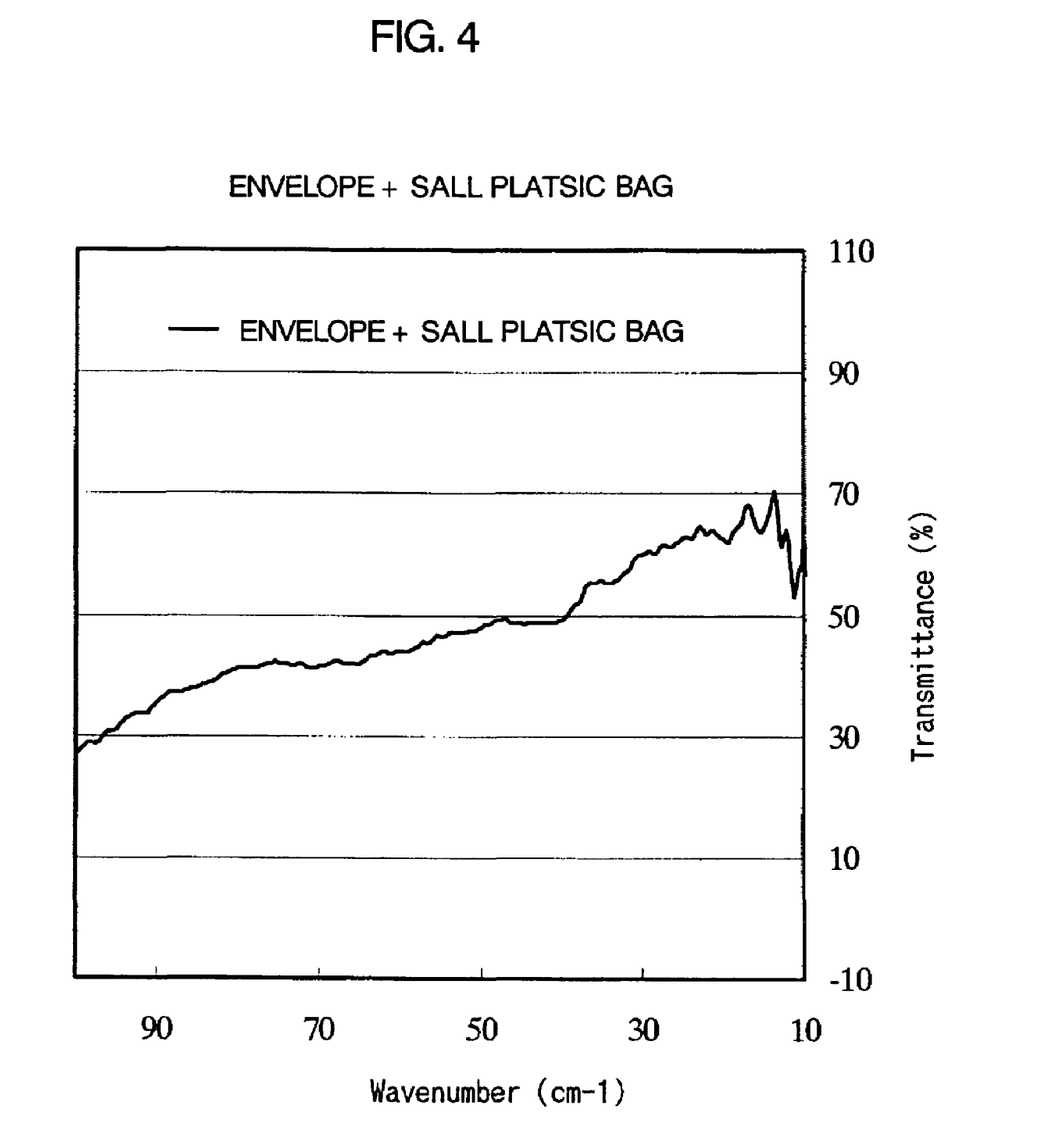
FIG. 4 shows characteristics of a fingerprint spectrum of a mixture of an envelope and a plastic bag.
Figure 5:
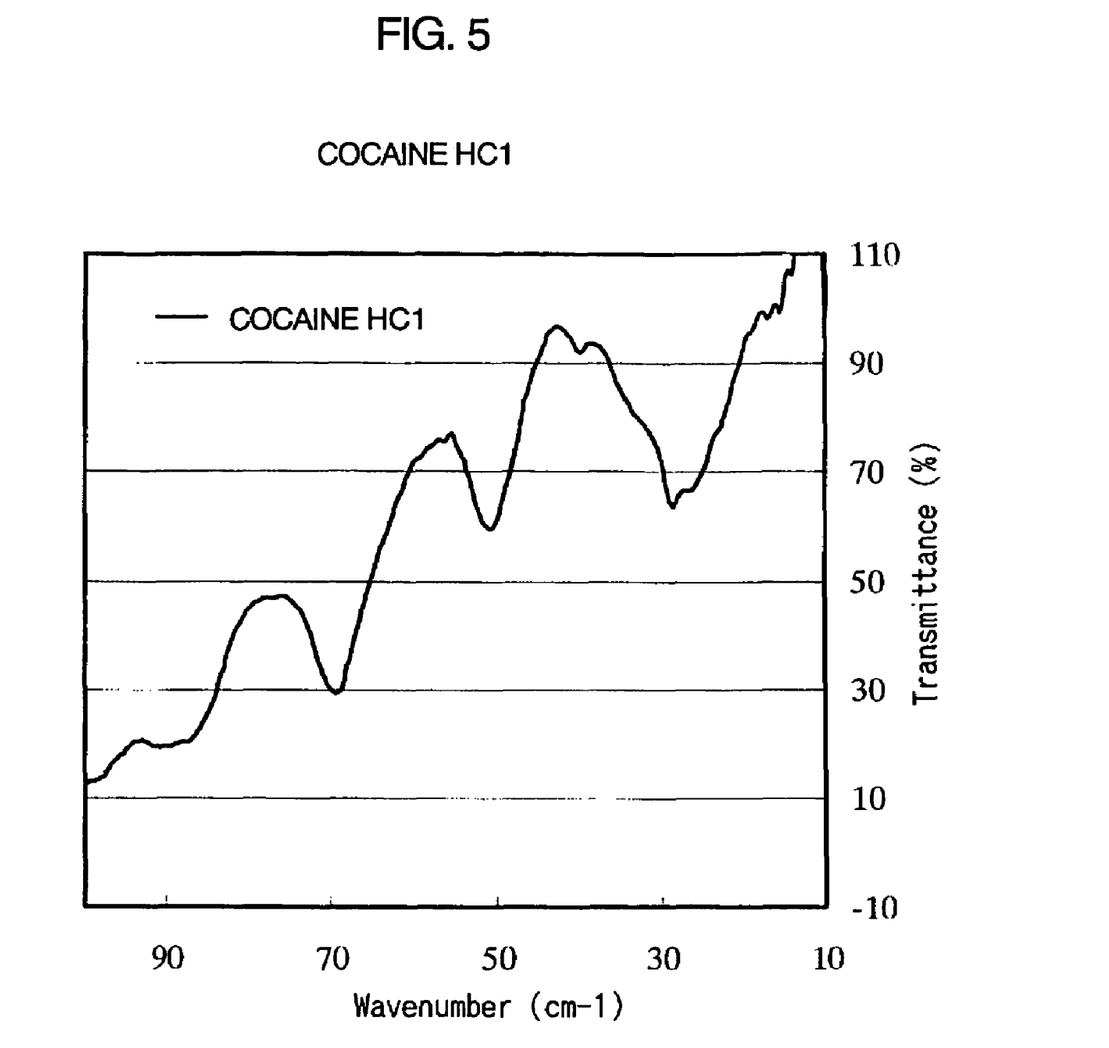
FIG. 5 shows characteristics of a fingerprint spectrum of a cocaine HCl.
Figure 6:
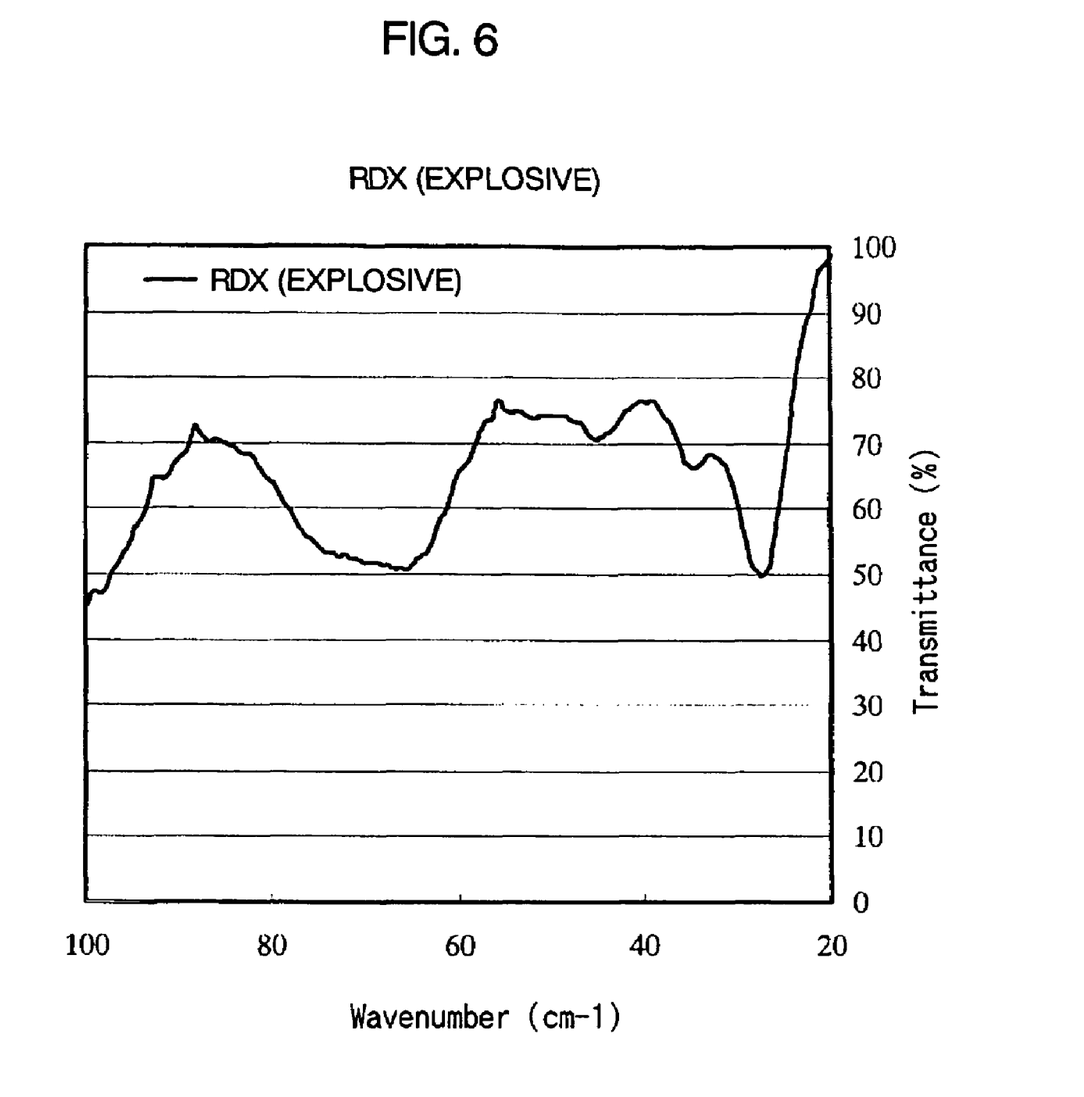
FIG. 6 shows characteristics of a fingerprint spectrum of an RDX.

Next, standard spectrum data stored in the database in the hard disk of the personal computer 60 will be described with reference to FIGS. 4, 5 and 6. FIGS. 4, 5 and 6 show characteristics of absorption spectra of the detecting target materials, respectively.

Specifically, FIG. 4 shows a absorption spectrum of a mixture of an envelope and a small polyethylene bag, FIG. 5 shows an absorption spectrum of cocaine HC1, and FIG. 6 shows an absorption spectrum of RDX. Based on the spectrum data of FIGS. 4, 5 and 6, standard spectrum data is formed.

The above-mentioned absorption spectra exhibit characteristics different between the respective materials as the human fingerprints are different between individuals. For this reason, hereinbelow, the above-mentioned absorption spectrum is referred to as a fingerprint spectrum.

To obtain the fingerprint spectra of FIGS. 4, 5 and 6 in advance, the material inspecting apparatus 1 applies a tera-hertz wave to the detecting target materials, and measures the output waves. In FIGS. 4, 5 and 6, the horizontal axis indicates the number of wavelengths included in the length of 1 cm, and the vertical axis indicates the transmittance.

In this example, a plurality of tera-hertz waves of different frequencies are applied to the detecting target material to obtain plural transmittances corresponding to the respective frequencies. The thus-obtained transmittances are linearly arranged to form the standard spectrum data. The obtained standard spectrum data is stored in the database for each of the detecting target materials.

In the first embodiment of the present invention, an detecting target material in the inspecting object is cocaine HC1 and RDX while the envelope and the plastic bag are adjunct materials. In other words, in the first embodiment, the cocaine HC1 and RDX are enclosed in the envelope and the plastic bag, and when detecting the cocaine HC1 and RDX enclosed in the envelope, the cocaine HC1 and RDX are detected without opening the envelope.

As understood from comparison of spectra data of FIGS. 4, 5 and 6, the fingerprint spectrum (adjunct spectrum) of the mixture of the envelope and the plastic bag has a small change in the transmittance with respect to the change in the frequency. On the other hand, the fingerprint spectra of the cocaine HC1 and the RDX have a large change in the transmittance with respect to the change in the frequency. In other words, the cocaine HC1 and the RDX have characteristics of strong dependence of the transmittance on the frequency (wavelength).

Accordingly, it is possible to detect the cocaine HC1 and the RDX without using the fingerprint spectra of the envelope and the plastic bag. However, by using the fingerprint spectra of the envelope and the plastic bag, it is possible to improve the detecting performance of the cocaine and the RDX.

By the above-described configuration, based on the measurement of the output wave, it becomes possible to determine whether or not the inspecting object includes the target material that has the standard spectrum stored in the database.

Figure 7:
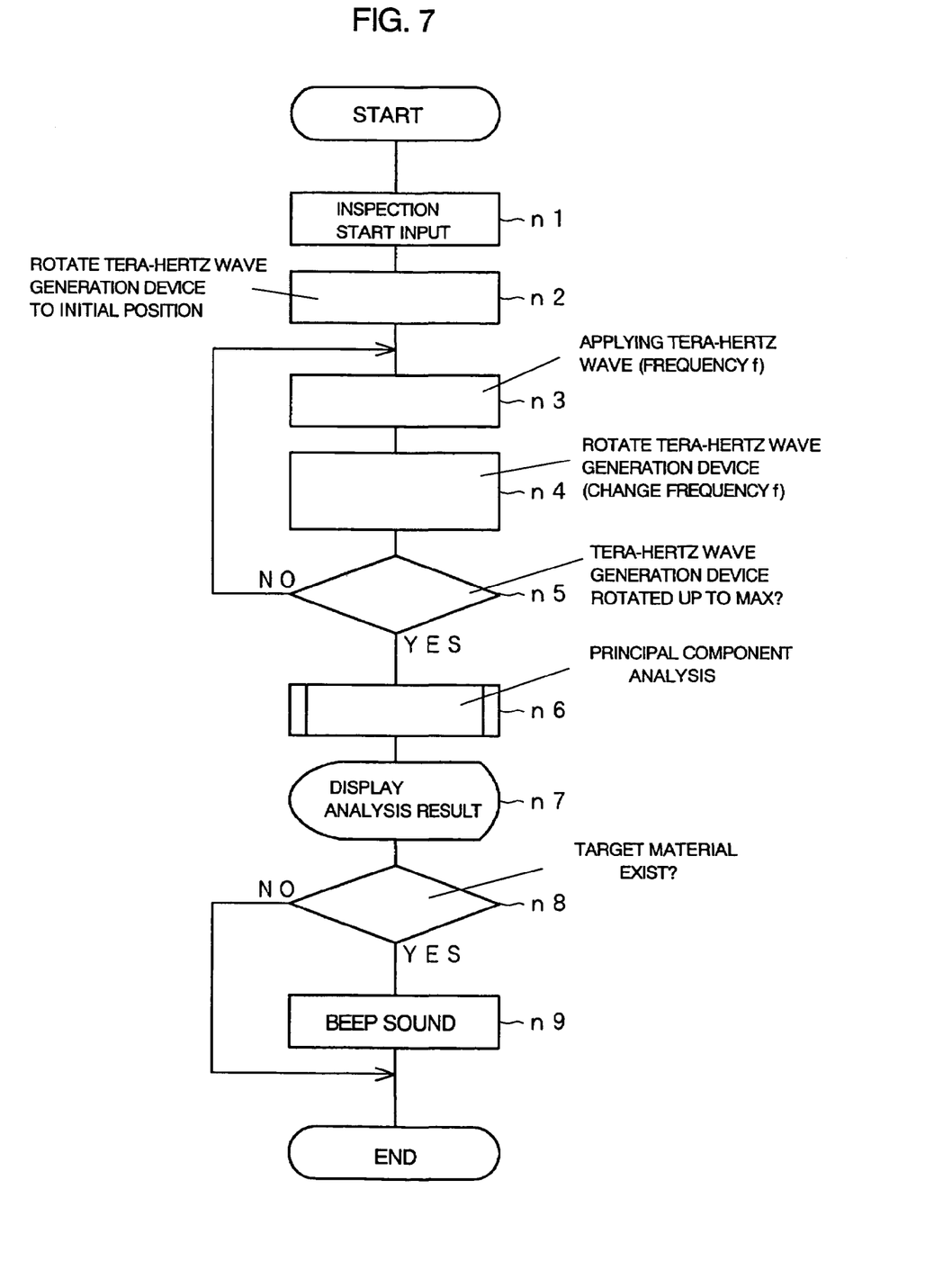
FIG. 7 is a flowchart showing a detecting process operation performed by a control device of a personal computer.

Next, a procedure of the detecting processes will be described with reference to a flowchart of FIG. 7. The control device of the personal computer 60 performs the detecting processes in accordance with a material detecting program stored in the database.

When an operator operates a detecting start button by means of the touch monitor 4 at Step n1, the control device rotates the tera-hertz wave generation device 20 to an initial position at Step n2.

At Step n3, the control device causes the pump wave injection device 11 to start to generate a pump wave so that a tera-hertz wave can be applied to an inspecting object 9, and the detector 50 can measure the output wave at Step n3. After applying the tera-hertz wave to the inspecting object 9 and measuring the output wave, the control device rotates the tera-hertz wave generation device 20 at Step n4. By this rotation of the tera-hertz wave generation device 20, the frequency f of the tera-hertz wave to be applied to the inspecting object 9 is changed.

When measuring the output wave at Step n3, the noise is cancelled by using the reference wave.

At Step n5, until the rotated angle of the tera-hertz wave generation device 20 reaches the maximum value MAX, the control device repeatedly performs the processes of Steps n3 and n4 so that the tera-hertz wave with the changed frequency can be applied to the inspecting object 9 one after another, and the output wave can be repeatedly measured by the detector 50.

When reaching the maximum value of the rotated angle, a principal component analysis is performed based on the measured output waves at Step n6 to determine a material contained in the inspecting object 9.

The number of the tera-hertz wave frequencies that are changed by the angle rotation and are used for irradiating the inspecting object 9 is equal to or larger than the number of the fingerprint spectra (i.e., the mixture of the envelope and plastic bag, the cocaine HCl and the RDX in this example) that are stored in the database.

In the principal component analysis, matrix calculation by a least square method is performed, using the fingerprint spectra shown in FIGS. 4, 5 and 6 to obtain a result of the analysis. This calculation is performed in units of frequencies.

Specifically, when "I" designates the output wave, "S" designates the standard spectrum, and "P" designates the concentration of the material indicated by the output wave, the following equation (5) can be established.

$$[I]=[S][P] \tag{5}$$

When the number of the detecting materials is "M", the tera-hertz waves of frequencies of which number is "N" are used to measure the output wave E so that the following linear matrix equation (6) can be established.

$$\begin{bmatrix} I(1,1) \\ \vdots \\ I(N,1) \end{bmatrix} = \begin{bmatrix} S(1,1) & \cdots & S(1,M) \\ \vdots & \vdots & \vdots \\ S(N,1) & \cdots & S(N,M) \end{bmatrix} \begin{bmatrix} P(1,1) \\ \vdots \\ P(M,1) \end{bmatrix} \tag{6}$$

In the equation (6), since the matrix [S] is known from the standard spectra, and the matrix [I] is known from the output wave E, the matrix [P] can be obtained by the calculation.

When the equality N=M is satisfied, the matrix [P] can be obtained using the following the equation (7).

$$[P]=[S]^{-1}[I] \tag{7}$$

When the inequality N>M is satisfied, the matrix [P] can be obtained by the least square method, using the following equation (8).

$$[P]=([S]^t[S])^{-1}[S]^t[I] \tag{8}$$

The matrix [P] can be obtained by solving the above equations. That is, the concentration of the detecting target material contained in the inspecting object can be obtained, so that it is possible to determine whether or not each detecting target material exists in the inspecting object. One example of the detecting condition is that when the concentration of the detecting target material is no less than 50 percent, it is determined that the detecting target material exists in the inspecting object. The data of such a detecting condition is stored as determination base data in the database of the personal computer 60 to perform the determination using the determination base data.

In the first embodiment of the present invention, the detecting materials are the mixture of the envelope and plastic bag, the cocaine HC1, and the RDX, that is, the number "M" of the detecting materials is "3". Accordingly, the calculation is carried out with the number "N" of the frequencies being equal to or larger than the number "M" of the detecting materials.

When carrying out the calculation, an appropriate weighting factor is preferably applied to the standard spectrum to enhance the detecting accuracy.

The result of the principal component analysis is obtained in the form of numerical values that indicate the percentage of the contained detecting target material corresponding to the fingerprint spectrum stored in the hard disk. This analysis result (detected result) obtained in the form of the numerical values is displayed on the touch monitor 4 as shown in FIG. 8 at Step n7.

Figure 8:
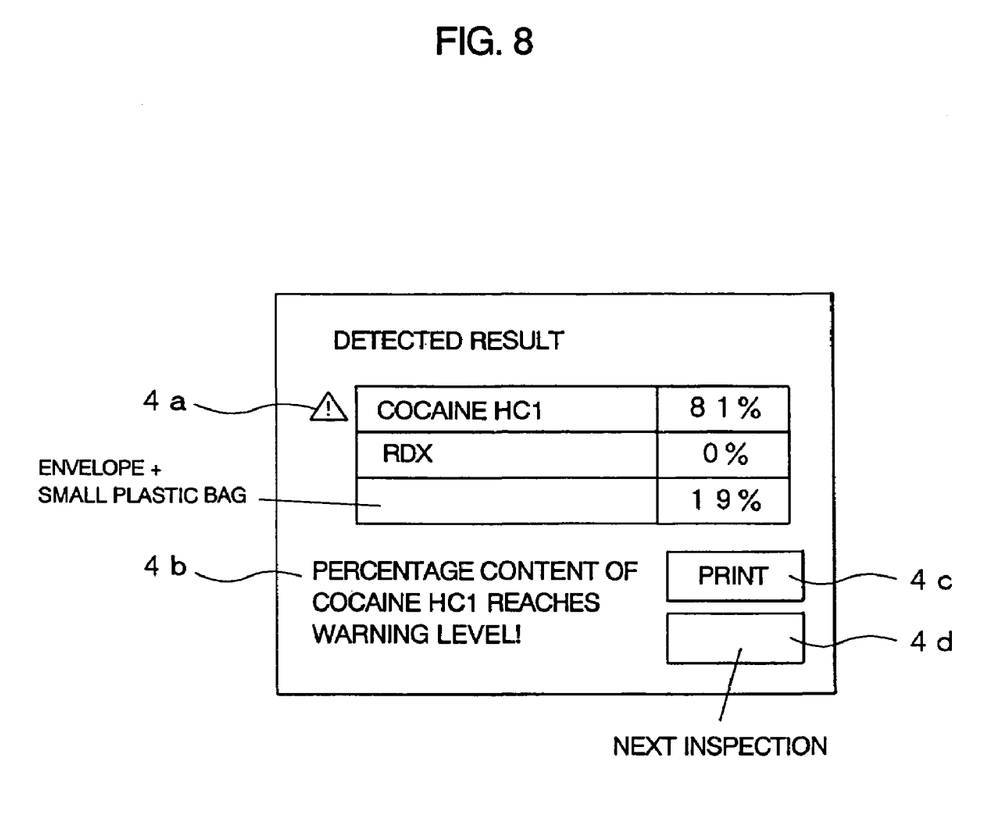
FIG. 8 shows a detected result image displayed on a monitor.

FIG. 8 shows an example of a detected result image displayed on the monitor. In FIG. 8, the percentages of the detecting materials are shown. When the percentage of the detecting target material is equal to or larger than a predetermined value, a warning mark 4a is displayed at the left side of the cocaine HC1, for example, and a warning message is also displayed to give notice to an operator.

A printing button 4c is displayed for printing the currently displayed detected result together with the detecting data and time, and a next detecting button 4d is displayed for discarding (or storing) the currently displayed detected result to carry out a next detecting operation.

When any of the detecting target materials exists as shown in FIG. 8 at Step n8 (or a percentage of any of the detecting target materials is equal to or larger than a predetermined value), a beep sound is generated from a speaker at Step n9. On the other hand, when no detecting target materials are detected, the detecting operation is finished.

According to the above-described operation, a tera-hertz wave is applied to a specified point of the inspecting object while gradually changing the frequency of the tera-hertz wave. In this manner, the fingerprint spectrum of the output wave can be obtained. Thereby, the percentage content of the fingerprint spectrum of the detecting target material can be determined so that the existence of the detecting target material can be reliably detected without breaking or opening the inspecting object.

The detecting operation is performed only on the specified point, so that the detecting operation can be promptly finished.

Further, when it is determined that the detecting target material exists, this existence is notified to an operator by the warning mark, the warning message and the beep sound. Accordingly, it is possible to detect the existence of the detecting target material in a uniform manner without depending on ability of an operator.

In addition, the determination of whether or not the detecting target material exists is performed by the control device of the personal computer 60. Accordingly, when the fingerprint spectrum of the output wave is obtained, the determination of the existence and the absence of the detecting target material can be performed at a high speed. As a result, baggage inspection and air mail inspection at an air terminal, for example can be promptly performed without delay.

It is possible, therefore to reliably prevent banned materials (stimulant drug and narcotic drug) and dangerous materials (explosives such as an RDX and a TNT) from being imported and exported, by the speedy inspection without giving a trouble to international air passengers. Moreover, it is possible to efficiently inspect a large amount of mails at a mail office and so on.

In the first embodiment of the present invention, the frequency of the tera-hertz wave is changed by rotating the tera-hertz wave generation device 20. Alternatively, a plurality of the tera-hertz wave generation devices 20 may be provided with the material inspecting apparatus 1 such that different frequencies of the tera-hertz waves are set in the respective tera-hertz wave generation devices 20. In this case, the tera-hertz waves having the different frequencies may be simultaneously applied to the inspecting object 9, or may be applied to the inspecting object 9 in turn.

In the case where a plurality of the tera-hertz wave generation devices 20 are provided, it is possible to perform the detecting operation at a higher speed than in the first embodiment. When the tera-hertz waves of the different frequencies are simultaneously applied to the inspecting object 9, the received output wave is preferably divided into the frequencies of the tera-hertz waves.

Furthermore, a re-detecting-button may be displayed on the monitor in FIG. 8. When the re-detecting button is operated, the detecting operation is performed again such that the previous detected percentage content and the current detected percentage content both are displayed.

In this case, when a detected result is suspicious, the position of the inspecting object is shifted by a small length, for example. Then, the detecting operation is performed again with the position of the inspecting object being changed. When obtaining the re-detected result, the existence and absence of the detecting target material is determined based on the total detected result.

Furthermore, without providing the material inspecting apparatus 1 with the collective lens 41 and the dispersion lens 42, the tera-hertz wave may be applied to the inspecting object with the tera-hertz wave being not focused. Thereby, the cost of the material inspecting apparatus 1 can be reduced.

In the first embodiment of the present invention, the banned materials set as the detecting target materials are cocaine HC1 and the RDX. However, the banned materials may be a stimulant drug (ephedorine, amphetamine, for example) 2C-B, HCI, morphine, a hallucinatory, an MDA, an MDMA and the like. Thus, many banned materials may be set as the detecting target materials, and fingerprint spectra of these banned materials may be stored in the hard disk.

Further, in the first embodiment of the present invention, the fingerprint frequency of the mixture of the envelope and the plastic bag is used as the adjunct spectrum of the adjunct material. However, the fingerprint spectrum of the adjunct envelope and the fingerprint spectrum of the adjunct plastic bag may be separately used as the adjunct spectra. In addition, fingerprint spectra of other materials such as cloth and paper may be stored as adjunct spectra of the adjunct materials in database in the hard disk.

Accordingly, since the number of the stored fingerprint spectra is increased, detecting accuracy in the principal component analysis can be enhanced. In addition, since the number of the detected materials is increased, the performance of the detecting operation can be improved.

In some cases, when the fingerprint spectrum of the detecting target material contained in the inspecting object 9 is detected, the percentage content of this fingerprint spectrum is different from that of the standard spectrum measured at the time of obtaining this standard spectrum for the database. In such a case, the similarity of the characteristics of the fingerprint spectrum and the standard spectrum is taken into account, and the concentration difference is estimated in order to detect the detecting target material. Thereby, it is possible to reduce the number of the standard spectra stored in the database, and to shorten the time required for the calculation.

Further, for a material of which fingerprint spectrum is changed depending on a material state such as a particle size, a plurality of standard spectra corresponding to respective material states may be prepared separately.

Thereby, it is possible to reliably detect the detecting target material regardless of the material states including powder, particle, plate states, and to improve a detecting accuracy.

Moreover, the above-described detecting operation may be a main detecting operation, and a preliminary detecting operation may be performed before the main detecting operation. When performing the preliminary detecting operation, tera-hertz waves of two different frequencies are used for performing continuous differential measurement to detect the material having high absorption dependence on a wavelength. By the preliminary detecting operation, the existence of the detecting target material having high absorption dependence on a wavelength can be easily detected at a high speed while the envelope and the plastic bag are not detected. When detecting the detecting target material having high absorption dependence on a wavelength at the preliminary detecting operation, the main detecting operation is performed on this detecting target material. By this two stage detecting operation, it is possible to speed up the detecting operation, and to improve the detecting accuracy of the detecting operation.

In stead of rotating the tera-hertz wave generation device 20 by the rotation driving device 22, the pump wave generation device may be rotated around itself, or around the tera-hertz generation device 20. Also in this configuration, it is possible to change the pump wave incident angle to the tera-hertz wave generation device 20.

Figure 9:
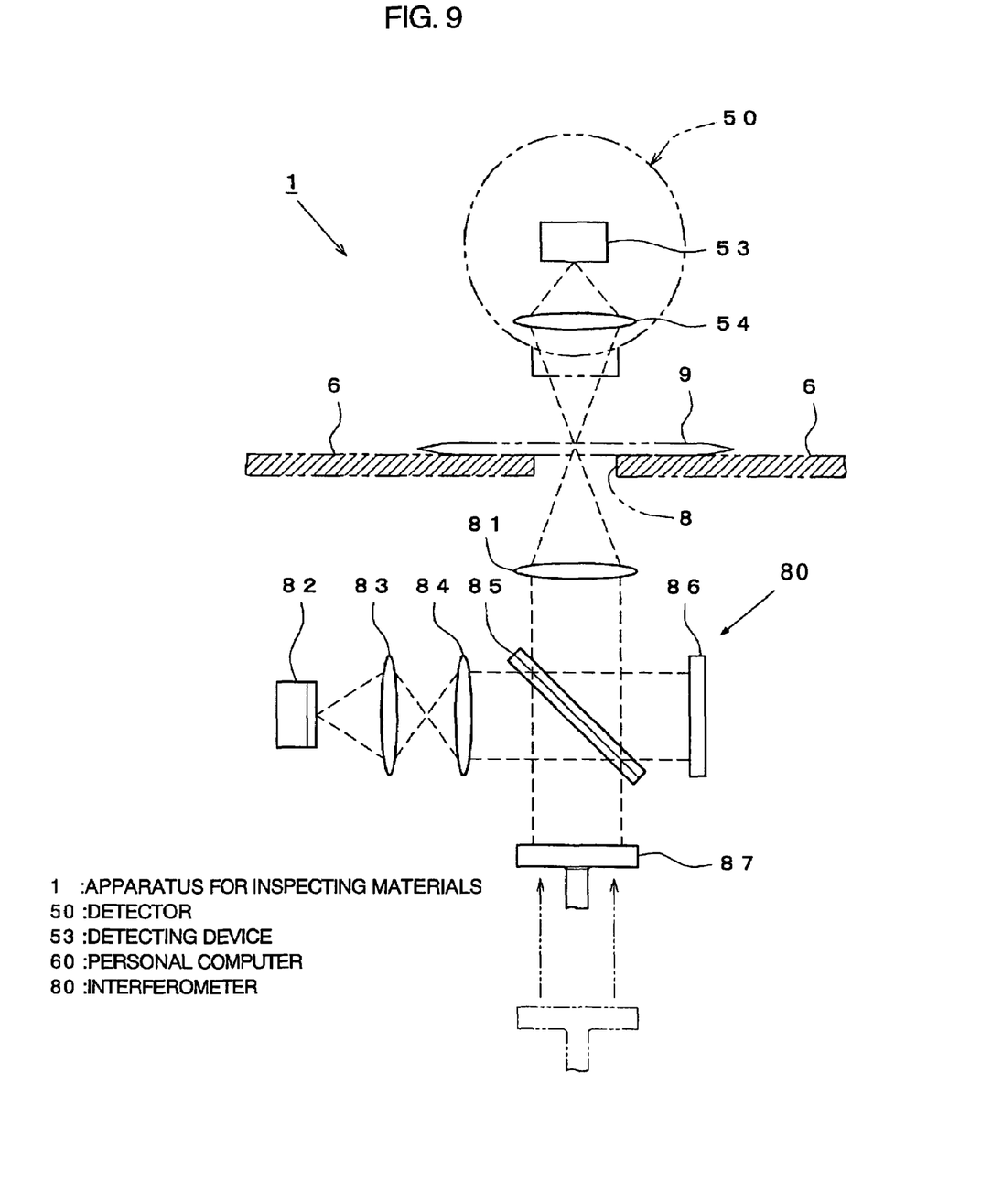
FIG. 9 shows a system configuration of a material inspecting apparatus according to a second embodiment of the present invention.

Next, a second embodiment of the present invention will be described with reference to FIG. 9. According to the second embodiment of the present invention, a tera-hertz wave generation device is constituted by a interferometer 80 that uses an FTIR (Fourier Transform Infrared Spectrometer). In this example, the interferometer 80 is a Michelson interferometer.

The interferometer 80 includes a collective lens 81, a light source 82, a condenser lens 83, a collimator lens 84, a beam splitter 85, a fixed mirror 86, and a moving mirror 87. The operation of the interferometer 80 will be described. First, radiation light is emitted from the light source 82, and is focused by the condenser lens 83. Then, the diameter of the focused light is enlarged by the collimator lens 84, and thereafter, the light from the collimator lens 84 arrives at the beam splitter 85.

The beam splitter 85 divides the arriving light into reflected light and penetrating light. Referring to FIG. 9, the reflected light that is reflected by the beam splitter 85 travels downwards, and the penetrating light that penetrates the beam splitter 85 travels in the right direction of FIG. 9.

Thereafter, the penetrating light is reflected by the fixed mirror 86, and the reflected light is reflected by the moving mirror 87. As a result, both of the penetrating light and the reflected light return to the surface of the beam splitter 85.

At the optical position of the beam splitter with respect to the moving mirror 87 where the optical length of the light reflected by the fixed mirror 86 becomes equal to the optical length of the light reflected by the moving mirror 87, that is, where the relative optical length difference between both of the reflected light from the fixed mirror 86 and the moving mirror 87 becomes zero, interfering on the surface of the beam splitter 85 between both of the reflected light occurs with the phases of both of the reflected light being equal for the all wavelength components included in both of the reflected light so that the interfered light having the strongest amplitudes can appear.

When the moving mirror 87 is moved, the optical length of the light reflected by the fixed mirror 86 becomes different from the optical length of the light reflected by the moving mirror 87. Thereby, interfering on the surface of the beam splitter 85 between both of the reflected light occurs with the phases of both reflected light being different for the respective wavelength components. As a result, the intensity of the interfered light is reduced.

Half of the interfered light travels toward the light source 82 to be lost, and the remaining half of the interfered light is guided upwards, to enter the collective lens 81. The interfered light that has entered the collective lens 81 is applied to the inspecting object 9, and then arrives at a detecting device 53 via a detecting lens 54 provided in a detector 50.

By the above-described operation and configuration, the tera-hertz wave of the white light having a plurality of wavelengths is applied from the collective lens 81 to the inspecting object 9 on the board 6, and is then received by the detecting device 53.

In order to detect the spectrum components, the background measurement and the sample measurement are performed. The background measurement is performed in a condition where the inspecting object 9 is not placed on the board 6, and the sample measurement is performed in a condition where the inspecting object 9 is placed on the board 6. Then, Fourier transformation of the results of the background and sample measurements is performed by the personal computer 60. Next, the data of Fourier transformation of the background measurement is compared to the sample measurement to obtain the target spectrum.

Additionally, the detecting device 53 may be constituted by an Si bolometer. In this case, the detector 50 of the first embodiment can be used.

The configuration of the present invention corresponds to the configuration of the above-described embodiments as follows.

The apparatus for detecting materials corresponds to the material inspecting apparatus 1 of the above embodiments.

Similarly, the predetermined position corresponds to the part of the inspecting object 9 that swells, the oscillator is the pump wave injection device 11, the tera-hertz wave applying means is the tera hertz generation device 20 and the interferometer 80, the output wave receiving means is the detector 50, the spectrum obtaining means is the detecting device 53 and the personal computer 60, the white light applying means is the interferometer 80, and the output wave is the output wave E.

Further, the detecting material corresponds to the cocaine HC1, the RDX, and the mixture of the envelope and the plastic bag, the detecting target material the cocaine HC1 and the RDX, and the adjunct material the mixture of the envelope and the plastic bag.

Furthermore, the detecting spectrum corresponds to the standard spectrum. The detecting target spectrum corresponds to the fingerprint spectra of the cocaine HCl and the RDX, the adjunct spectrum the mixture of the envelope and the plastic bag.

Further, the determining means corresponds to the control device of the personal computer 60.

However, the configuration of the present invention is not limited to the configuration of the first and second embodiments, and other configuration can be adopted without departing from the scope of the present invention.

What is claimed is:

1. A method for detecting materials, comprising the steps of:
    applying tera-hertz waves of a plurality of different frequencies around a boundary between a light wave frequency and a radio wave frequency to a predetermined position of an inspecting object by using a tera-hertz wave applying means; and
    detecting the presence or absence of a detecting material by determining whether or not an output wave includes a detecting spectrum of the detecting material, wherein the output wave is the tera-hertz wave that has been applied to the inspecting object,
    wherein the tera-hertz wave applying means includes white light applying means for applying white light of a plurality of different frequencies to the inspecting object, and wherein a spectrum obtaining means for performing Fourier transformation on the output wave to obtain a spectrum formed by the respective different frequencies is used to receive the output wave and to determine whether or not the output wave includes the detecting spectrum of the detecting material.

2. A method for detecting materials according to claim 1, further comprising the steps of:
    setting as the detecting spectrum a detecting target spectrum of the detecting target material and an adjunct spectrum of an adjunct material; and
    determining whether or not the output wave includes the adjunct spectrum along with the detecting target spectrum.

3. An apparatus for detecting materials, comprising:
    a database for storing detecting spectra of detecting materials;
    tera-hertz wave applying means for applying tera-hertz waves having a plurality of different frequencies around a boundary between a light wave frequency and a radio wave frequency, to a predetermined position of an inspecting object;

output wave receiving means for receiving an output wave that is the tera-hertz wave having been applied to the inspecting object; and determining means for determining whether or not the output wave includes the detecting spectrum, wherein the tera-hertz wave applying means includes white light applying means for applying white light of a plurality of different frequencies to the inspecting object, and the apparatus further includes spectrum obtaining means for performing Fourier transformation on the output wave to obtain a spectrum formed by the respective different frequencies.

4. An apparatus for detecting materials according to claim 3, wherein the detecting spectra include a detecting target spectrum of a detecting target material and an adjunct spectrum of an adjunct material.

5. A method for detecting materials according to claim 1, further comprising the step of:

displaying a detected result when the output wave includes the detecting spectrum.

* * * * *